(12) United States Patent
Schmid et al.

(10) Patent No.: US 9,395,343 B2
(45) Date of Patent: Jul. 19, 2016

(54) RESONANT FIBER BASED AEROSOL PARTICLE SENSOR AND METHOD

(71) Applicant: DANMARKS TEKNISKE UNIVERSITET, Kgs. Lyngby (DK)

(72) Inventors: Silvan Schmid, Copenhagen S (DK); Anja Boisen, Birkerød (DK)

(73) Assignee: Danmarks Tekniske Universitet, Kgs. Lyngby ( * ) Notice: Subject to any disclaimer, the term of this patent is extended or adjusted under 35 U.S.C. 154(b) by 232 days.

(21) Appl. No.: 14/356,059

(22) PCT Filed: Nov. 2, 2012

(86) PCT No.: PCT/DK2012/050405
§ 371 (c)(1),
(2) Date: May 2, 2014

(87) PCT Pub. No.: WO2013/064157
PCT Pub. Date: May 10, 2013

(65) Prior Publication Data
US 2014/0305191 A1    Oct. 16, 2014

Related U.S. Application Data

(60) Provisional application No. 61/555,644, filed on Nov. 4, 2011.

(30) Foreign Application Priority Data

Nov. 4, 2011 (EP) .................................... 11187856

(51) Int. Cl.
*G01N 29/02* (2006.01)
*G01N 33/00* (2006.01)
(Continued)

(52) U.S. Cl.
CPC .............. *G01N 33/0004* (2013.01); *G01N 5/02* (2013.01); *G01N 9/002* (2013.01);
(Continued)

(58) Field of Classification Search
CPC .......... G01N 29/022; G01N 2291/014; G01N 2291/0256; G01N 29/036
See application file for complete search history.

(56) References Cited

U.S. PATENT DOCUMENTS 3,561,253 A    2/1971 Dorman
3,828,607 A    8/1974 Janzen et al.
(Continued)

FOREIGN PATENT DOCUMENTS

EP    1 361 428    11/2003
WO    WO2008/020903    2/2008

OTHER PUBLICATIONS

Fierz et al., "Real-time measurement of aerosol size distributions with an electrical diffusion battery", Aerosol Science, 33, 1049-1060, 2002.
(Continued)

*Primary Examiner* — David A Rogers
(74) *Attorney, Agent, or Firm* — Nixon Peabody LLP

(57) ABSTRACT

The present invention relates to methods and devices for determining the weight of small particles, typically being nano-sized particles by use of resonating fibers in the form of elongate members being driven into resonance by an actuator or e.g. thermal noise/fluctuation. The frequency shift in resonance frequency due to depositing of nano-sized particles is correlated with the mass deposited on the elongate member and the vibration frequency of the elongate member is determined by a detector. The read-out from the detector is transformed into a mass deposited on the elongate member. Particles are deposited by letting a fluid with the particles flow past the elongate member.

20 Claims, 5 Drawing Sheets

(51) Int. Cl.
*G01N 29/036* (2006.01)
*G01N 5/02* (2006.01)
*G01N 9/00* (2006.01)
*G01N 15/02* (2006.01)

(52) U.S. Cl.
CPC ......... *G01N 15/0255* (2013.01); *G01N 29/022* (2013.01); *G01N 29/036* (2013.01); *G01N 2291/0256* (2013.01); *G01N 2291/0427* (2013.01)

(56) References Cited

U.S. PATENT DOCUMENTS

| | | | |
|---|---|---|---|
| 4,041,768 A | 8/1977 | Gilbert et al. | |
| 4,446,720 A | 5/1984 | Sinclair | |
| 5,079,958 A | 1/1992 | Takase et al. | |
| 5,572,322 A | 11/1996 | Noda | |
| 6,803,840 B2 * | 10/2004 | Hunt | B82Y 10/00 205/766 |
| 6,823,720 B1 | 11/2004 | Adkins et al. | |
| 6,905,655 B2 * | 6/2005 | Gabriel | B82Y 15/00 204/193 |
| 7,053,520 B2 * | 5/2006 | Zetti | B82Y 10/00 310/309 |
| 7,278,297 B2 * | 10/2007 | Bauza | B82Y 15/00 73/105 |
| 7,762,121 B2 * | 7/2010 | Ng | B82Y 15/00 73/23.31 |
| 7,765,854 B2 * | 8/2010 | Schilowitz | G01N 29/022 436/518 |
| 8,087,151 B2 * | 1/2012 | Park | G01N 27/12 29/592.1 |
| 8,215,170 B2 * | 7/2012 | Tao | G01N 29/036 324/633 |
| 8,281,642 B2 * | 10/2012 | Lee | G01N 27/127 73/23.2 |
| 8,653,716 B2 * | 2/2014 | Hentz | G01C 19/56 310/309 |
| 2002/0178784 A1 | 12/2002 | Radke et al. | |
| 2004/0238367 A1 * | 12/2004 | Penner | B82Y 30/00 205/76 |
| 2005/0072213 A1 * | 4/2005 | Besnard | G01N 27/127 73/31.06 |
| 2006/0284218 A1 * | 12/2006 | Kaner | B82Y 10/00 257/288 |
| 2007/0023621 A1 | 2/2007 | Blick et al. | |
| 2008/0150556 A1 * | 6/2008 | Han | B82Y 15/00 324/693 |
| 2008/0297276 A1 * | 12/2008 | Jun | B82Y 15/00 333/186 |
| 2009/0288479 A1 * | 11/2009 | Woody | B01F 11/0088 73/105 |
| 2010/0013456 A1 * | 1/2010 | Montelius | G01G 3/16 324/76.51 |
| 2011/0179883 A1 * | 7/2011 | Zettl | B82Y 30/00 73/862.41 |
| 2011/0212535 A1 * | 9/2011 | Kaul | B82Y 30/00 436/149 |
| 2011/0221301 A1 * | 9/2011 | Hentz | G01C 19/56 310/309 |

OTHER PUBLICATIONS

Naik et al., Towards single-molecule nanomechanical mass spectrometry, DOI: 10.1039, Nature Nanotechnology 4, 445-450, 2009.
Schmid S. et al., "Particle mass spectrometry based on micro string resonators for the application in portable aerosol monitors", NMC 2011: The 8th International Nanamechanical Sensing Workshop, 2011, pp. 48-49.
Schmid S. et al., "Real-Time Particle Mass Spectrometry based on Resonant Micro Strings", Sensors, vol. 10(9), pp. 8092-8100, 2010.

* cited by examiner

RESONANT FIBER BASED AEROSOL PARTICLE SENSOR AND METHOD

CROSS-REFERENCE TO RELATED APPLICATIONS

This application is a U.S. National Stage of International Application No. PCT/DK2012/050405, filed Nov. 2, 2012, which claims the benefit of European Patent Application No. 11187856.7, filed Nov. 4, 2011, and of U.S. Provisional Patent Application No. 61/555,644, filed Nov. 4, 2011, all of which are incorporated herein by reference in their entireties.

FIELD OF THE INVENTION

The present invention relates to methods and devices for determining the weight of small particles, typically being nano-sized particles by use of resonating fibers in the form of elongate members being driven into resonance by an actuator or e.g. thermal noise/fluctuation. The frequency shift in resonance frequency due to depositing of nano-sized particles is correlated with the mass deposited on the elongate member and the vibration frequency of the elongate member is determined by a detector. The read-out from the detector is transformed into a mass deposited on the elongate member. Particles are deposited by letting a fluid with the particles flow past the elongate member.

BACKGROUND OF THE INVENTION

During recent years an increasing demand for detecting characteristics of aerosols has arisen. One of the more delicate issues in determining the characteristics of aerosols is determination of the weight of nano-sized particles due to inter alia the inherent small dimensions.

In a work presented by the inventors in *Real-Time Particle Mass Spectrometry Based on Resonant Micro Strings, Sensors* 2010, 10, 8092-8100 it has been shown that the weight of micro-sized particles arranged on a micro string by hand can be determined from the resonance frequency of the micro string. Further, Naik et. al. in Towards single-molecule nanomechanical mass spectrometry, DOI: 10.1039 disclose a system to determining weight of nano-sized particles where particles are delivered to a detector in vaccum by hexapole ion optics. However, such manual arrangement of nano-sized particles on micro strings or utilising vacuum in combination with ion optics appear impractical.

U.S. Pat. No. 5,572,322 discloses an apparatus that measures the diameter, relative concentration and weight of particles. The detection of scattered light produced when light is projected at particles drawn into a nozzle-shaped measuring space is used to measure particle diameter. Particle concentration is measured based-on variations in the intensity of transmitted light, and particle weight is measured based on changes in operating frequency of a crystal oscillator resulting from the adhesion of particles on the surface of the crystal oscillator.

However, the system according to U.S. Pat. No. 5,572,322 is prone to in-accurate measurements of the particle weight as the deflection of the aerosol and thereby also the particles will result in that lighter particles escapes deposition on the surface of the crystal oscillator and only the heavier ones will deposit on the surface of the crystal oscillator.

WO2008/020903 disclose a method for detection of airborne biological agent using a self-exciting, self-sensing piezoelectric sensor that includes a piezoelectric layer and a non-piezoelectric layer. A recognition entity is placed on one or both layers. The antibody that recognizes and binds to the airborne species may be chemically immobilized on the cantilever sensor surface. Further, an analyte attractor is applied to the non-piezoelectric portion of the sensor, the attractor being specific to an analyte. Thus, the deposition of substance on the sensor according to WO2008/020903 is limited to know, specific substances which is attracted to the surface of a recessed sensor and the sensor is not applicable to determine the weight of e.g. unknown airborne substances.

Thus, while different measurement techniques are suggested to measure the weight of nano sized particles, they still suffer from the drawback of measuring in a practical manner the weight of representative, i.e. not only heavier ones, nano-sized particles.

Hence, an improved device and method for determining the weight of nano-sized particles of an aerosol would be advantageous, and in particular a more efficient and/or reliable device and method for determining such weights would be advantageous.

OBJECT OF THE INVENTION

It is a further object of the present invention to provide an alternative to the prior art.

In particular, it may be seen as an object of the present invention to provide a method and a device that solves the above mentioned problems of the prior art with respect to predictable measurements.

SUMMARY OF THE INVENTION

Thus, the above described object and several other objects are intended to be obtained in a first aspect of the invention by providing a method for determining the weight of aerosol particles. The method preferably utilises a sensor system comprising a sensor element having a base member and one or more elongate members, wherein each of the one or more elongate members are made from an elastic material with a longitudinal extension being at least ten times the diameter or the equivalent diameter of the cross section of the elongate member, each of the one or more elongate members being attached to the base member at at least one end or at a nodal point of the vibrational displacement through a connection and extends in a straight manner out from the base member, so as not to extend along and above the surface of the base member.

The sensor system may preferably further comprises an actuator for driving the one or more elongate members into mechanical resonance, and a detector for determining the vibration frequency of the one or more elongate members.

The method may preferably comprise the step of producing a flow of aerosol past one or more of the elongate member in an oblique direction, such as perpendicular, to the longitudinal direction of the elongate member, the flow of aerosol being parallel past the elongate member vibrating and detecting vibration frequency of the elongate member by use of the actuator and detector, so as to determine resonance frequency and determining the weight of the aerosol particles from the detected resonance frequency.

In accordance with the first aspect of the invention, the diameter or equivalent diameter of the elongate member(s) is advantageously in the range of 1 nm to 100 μm.

Furthermore, the velocity of the flow of aerosol past the one or more elongate members is preferably set sufficiently high to secure that deposition of the particles on the elongate member(s) is caused by inertial impaction. This advantageously means that the velocity of the aerosol produced is higher than 1 m/s. It is noted, that although deposition caused by intertial impaction is the dominant way of deposition at velocities >1 m/s, some deposition may still be caused by diffusion. By dominant is meant that the deposition rate of one collection mechanisms is at least 5 times higher than the deposition rate of the other collection mechanism.

In the case of electrostatic precipitation of charged nanoparticles on a counter-charged elongate member—that is, the electrostatic elongate member(s) being electrostatic charged to attracts electrostatic charged nanoparticles—the aerosol velocity may be smaller than 1 m/s.

In accordance with the various aspects and embodiments of the present invention, a minimal deflection of the streamlines of the flow past the elongate member(s) is aimed at. To accomplish this, the various aspects and embodiments of the invention advantageously comprise a region immediate downstream elongate member(s) devoid of obstacles. The extension of such a region being at least 100-1,000 diameters or equivalent diameters of the elongate member(s).

Thus, the region devoid of obstacles describe a 3-dimensional void with a face facing upstream and being perpendicular to the incoming flow of aerosol and a face facing downstream in a distance from the elongate member(s) being at least 100-1,000 diameters or equivalent diameters. No obstacles means that no physical objects are situated in the region, which could change the course of the streamlines downstream of the elongate member(s).

Furthermore, such a region may also be provided upstream of the elongate members, in which case such a region devoid of obstacles describe a 3-dimensional void with a face facing downstream and being perpendicular to the incoming flow of aerosol and a face facing upstream in a distance from the elongate member(s) being at least 100-1,000 diameters or equivalent diameters.

In many preferred embodiments, the elongate member(s) are arranged in a region of the flow of aerosol wherein the flow of aerosol being at least substantially free-streaming. This preferably means that the flow in the region where the elongate member is arranged may be described as being substantially parallel and inviscid, as well known to a skilled person. Preferably, this is obtained by arranging the elongate member outside viscous boundary layer(s) and/or cavities generating viscous flow and/or circulation flow.

In a second aspect, the invention relates to a through flow measuring device for measuring weight of aerosol particles contained in an aerosol flowing through the device. The device comprising a sensor through which the aerosol flows, and the sensor being arranged downstream of an inlet of the measuring device and the measuring device comprising a flow channel extending through the sensor. The sensor comprising one or more elongate members extending out from the boundaries of the flow channel in an oblique direction, such as perpendicular, to the flow direction of the fluid during use, and the flow channel being adapted to produce a parallel flow in the aerosol past the elongate member.

The sensor may preferable further comprise an actuator for driving the one or more elongate members into resonance, and a detector for determining the vibration frequency of the one or more elongate members, so as to determining the resonance frequency.

In a third aspect, the invention relates to a sensor element applicable in connection with the first and the second aspect of the invention. Further embodiments appear in the following disclosure and in the accompanying sub-claims.

Further details, embodiments and aspects of the invention are also presented in the claims.

In the present context terms have been used in a manner being ordinary to a skilled person. However, some of these terms are elaborated below:

Nano sized particles are preferably used to mean particles, such as solid particles or liquid droplets preferably having a diameter in the range of 1-100 nm and agglomerates of particles or liquid droplets. In relation to the present invention, it is noted that studies have disclosed that inhaled particles smaller than 100 nm elicit a significantly greater inflammatory response in the lungs of rats compared with larger particles with the same chemical composition. Therefore, particles with a diameter <100 nm are of particular interest from a nanoparticle sensor point of view.

Aerosol is preferably used to mean a suspension of nano and micro sized solid particles or nano and micro sized liquid droplets in a gas. Aerosol particles are preferably used to mean the particles of the aerosol.

Elastic material is preferably used to mean a material that deforms elastic before plastic deformation sets in with increasing strain.

Resonance frequency is preferably used to mean the natural frequency or the frequency at which the vibrational amplitude has a maximum.

Equivalent diameter is preferably used to mean a dimension of an elongate member when the cross section geometry is not circular and is determined by the square root of (4 times the area of the cross section divided by pi).

Fluid is preferably understood broadly an includes liquid and gas.

The present invention is found to be of particular use within the fields of:

Nanoparticle producing industry (cosmetics, paint, food, chemical, pharma, surface coating, etc) for work place safety Regulatory & health organizations for epidemiological nanoparticle measurements Cleanroom operators for measuring the particle concentration Private persons for personal protection Cities and country officials for air pollution monitoring Universities & scientific groups working in nanotechnology and aerosol related fields The first, second and third aspect of the present invention may each be combined with any of the other aspects. These and other aspects of the invention will be apparent from and elucidated with reference to the embodiments described hereinafter including the claims.

BRIEF DESCRIPTION OF THE FIGURES

The present invention and in particular preferred embodiments thereof will now be described in more detail with reference to the accompanying figures. The figures show ways of implementing the present invention and are not to be construed as being limiting to other possible embodiments falling within the scope of the attached claim set.

DETAILED DESCRIPTION OF PREFERRED EMBODIMENTS

Figure 1:
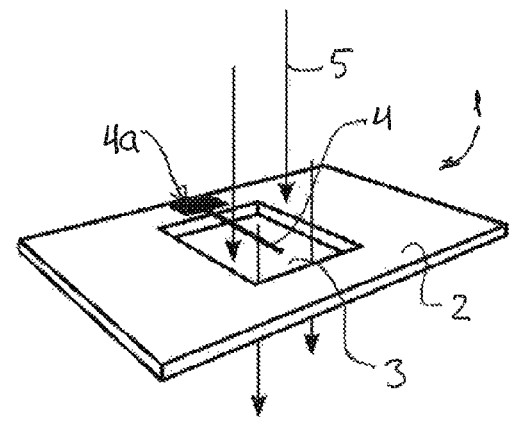
FIG. 1 shows schematically a sensor element according to a first embodiment of the invention.

FIG. 1 shows schematically a sensor element 1 according to a first embodiment of the invention. The sensor element 1 comprises a base member 2 having a square shaped penetration 3 forming a flow passage in the element 1. It is noted that the penetration may have other shapes than square shaped. An elongate member 4 is attached to the base member 2 at one distal 4a and extends from the base member 2 at least partially over the penetration 3. Thus, the elongate member 4 extends in a straight manner out from the base member 2, so as not to extend along and above the surface of the base member 2. Thereby, an incoming flow of e.g. an aerosol is able to flow past the elongate member 4 without flowing towards the base member 2 which could otherwise induce strong curvature in the stream lines—e.g. like an impinging jet flow situation—which results in uneven deposition of particles on the elongate member 4.

In many of the embodiments of the invention, the base element 2—or in general the part at which the elongate member 4 is arranged—often has a mass that is substantive higher than the weight of the elongated member 4, such as having a mass at least 100 or even 1,000 times higher. This results in the resonance frequency of the base element 2 and the resonance frequency of the elongate member 4 being substantially different and distinguishable from each other. Based on this and the fact that the resonance frequency of the elongate member 4 is used to measure the weight of nano-sized particles, the part of elongate member 4 which is not being fixed or otherwise attached to base member 2 is also referred to as a resonator.

An aerosol 5—or in general a fluid—with particles to be measured by weight is led by a suitable flow channel (as will be disclosed in greater details below) in a direction being oblique to, and preferably perpendicular, to the upper surface of the base member 2. In FIG. 1, the flow of the aerosol 5 is shown by straight arrows going through the penetration. Upper surface refers to the surface facing in upstream direction of the incoming aerosol 5 that is, with reference to FIG. 1, the surface facing upwardly.

It is noted, that the more relevant feature as to the direction flow is that the fluid is allowed to flow unhindered past elongate member 4 and less relevant that the flow is perpendicular to a base element 2; in particular as the base element is often not present in the flow path of a measuring device utilising the sensor element 1. Thus, the mutual orientation of the elongate member 4 and the flow direction is preferably that no obstacles are present downstream of the elongate member. No obstacles present downstream means preferably downstream to an extent of at least 100-1,000 diameters of the elongate member 4.

The elongate member 4 is made from a flexible material, typically selected from the group consisting of ceramics (e.g. silicon nitride, silicon carbide, silicon dioxide, zinc oxide, aluminium nitride, etc.), semiconductors (e.g. silicon, gallium arsenide, etc. . . . ), metals/elements (e.g. Al, Ni, Ti, Cr, Mo, W, Ni, Pd, PI, Cu, Ag, Au, Al, steel, etc. . . . ), alloys (e.g. TiW, NiCr, etc. . . . ), polymers (e.g. epoxies, SU-8, PS, PMMA, etc. . . . ), carbon materials (e.g. carbon nanotubes, graphene, graphite, etc. . . . ) and has preferably the following geometrical characteristics:

Length of the part of the elongate member being exposed to the fluid flow may be in the order of 1 µm-10 mm. Preferably, the length is in the order of 10 µm to 2 mm.

Cross sectional shape of the elongate member: arbitrary (square, round, triangular, rhombic, irregular).

Diameter of elongate member (when the cross section geometry is not circular, the diameter referred to as equivalent diameter and is determined by the square root of 4 times the area of the cross section divided by pi): 1 nm-100 µm, such as 10 nm-100 µm, or even 1 nm-50 µm. In some preferred embodiments, the elongate member is a carbon nanotube or nanowire. As indicated in the interval a narrow diameter is preferred in relation to the present invention.

It is often an aim of the invention to measure the amount of nano-sized particles in a representative sample of aerosol. The size of such a representative sample, varies with the amount of particles in the aerosol although it is envisaged that a typical airflow through a measuring device comprising a sensor element 1 is in the order of: 0.1 ml/min to 10 l/min, such as 1 m/s-100 m/s. However, the airflow will often be balanced with respect to the velocity of the aerosol. In many preferred embodiments according to the present invention, the flow past the elongate member(s) 4 is laminar, so as to avoid varying drag induced vibrations in the elongate member(s) 4 and/or turbulent disturbances in the deposition of particles.

Figure 9:
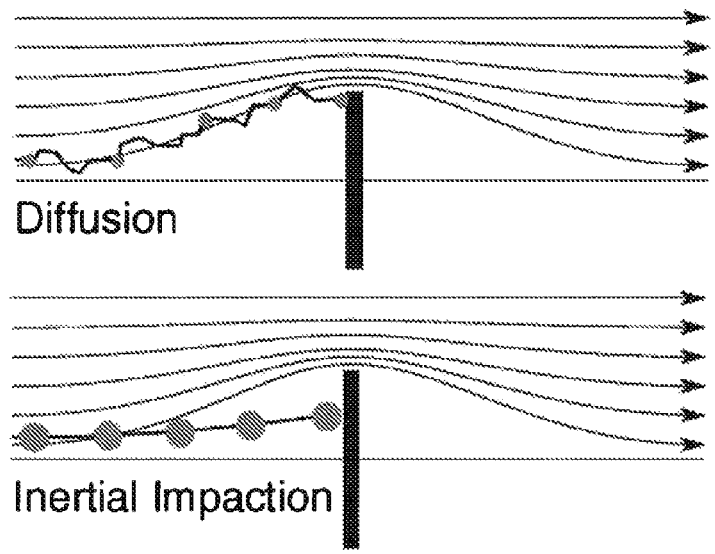
FIG. 9 shows schematically depositing of particles by diffusion (upper part of FIG. 9) and depositing of particles by inertial impact (lower part of FIG. 9)

During use, the elongate member 4 is resonating and as the aerosols flow past the elongate member 4, some of the aerosol particles deposit on the elongate member 4. The depositing of particles is typically provided by the following mechanisms:

Diffusion (see FIG. 9 upper part): Typically for particles with a diameter <300 nm Inertial impact (see FIG. 9 lower part): Typically for particles with a diameter >300 nm at an aerosol velocity of <2 m/s Electrostatic (particles and sensor elongate member are charged oppositely): Particles with a diameter typically in the between 1 nm-10 µm.

Interception

Gravitational settling

Such deposition will change the mass—at least locally—of the elongate member 4, resulting in a change in resonance frequency which is used to determine the mass of nano-sized particles.

The following generic formulas are found applicable for characterising the resonance of resonator (e.g. the part of the elongate member 4 not being attached to the base element 2):

Relative frequency resolution: $R = \Delta\Omega/\Omega_0$

Best achievable R at atmospheric pressure: $R = -1$ ppm

Total mass sensitivity: $S = -\Omega_0/(2m)$

The mass of the resonator is now defined by: $m <= -0.5 \Delta M/R$

Total added mass to the resonator corresponding to a large particle (e.g. a 10 micron gold particle): $\Delta M=10$ ng; Maximal resonator mass: $m<=5$ mg Total added mass to the resonator corresponding to a small particle (e.g. a 10 nm latex particle): $\Delta M=4$ ag. Maximal resonator mass: $m<=2$ pg Homogeneously distributed number of small particles (e.g. $100\times 10$ nm latex particle): $\Delta M=0.4$ fg; Maximal resonator mass: $m<=0.2$ ng In the above, $\Omega_0$ is the resonance frequency, m is the effective resonator mass, $\Delta\Omega$ is the frequency resolution, and $\Delta M$ is the mass resolution.

The determination of change in resonance utilises a detector that generates an output signal representing the frequency of vibration of the elongate member 4. The generation of the output signal typically involves a process by which a transducer (being the detector or forming part of the detector in an ordinary manner) converts one type of energy to another, that is, preferred devices according to the present invention includes transduction of resonating elongate members 4. Vibration of the elongate member 4 is performed by a suitable actuator.

Figure 5:
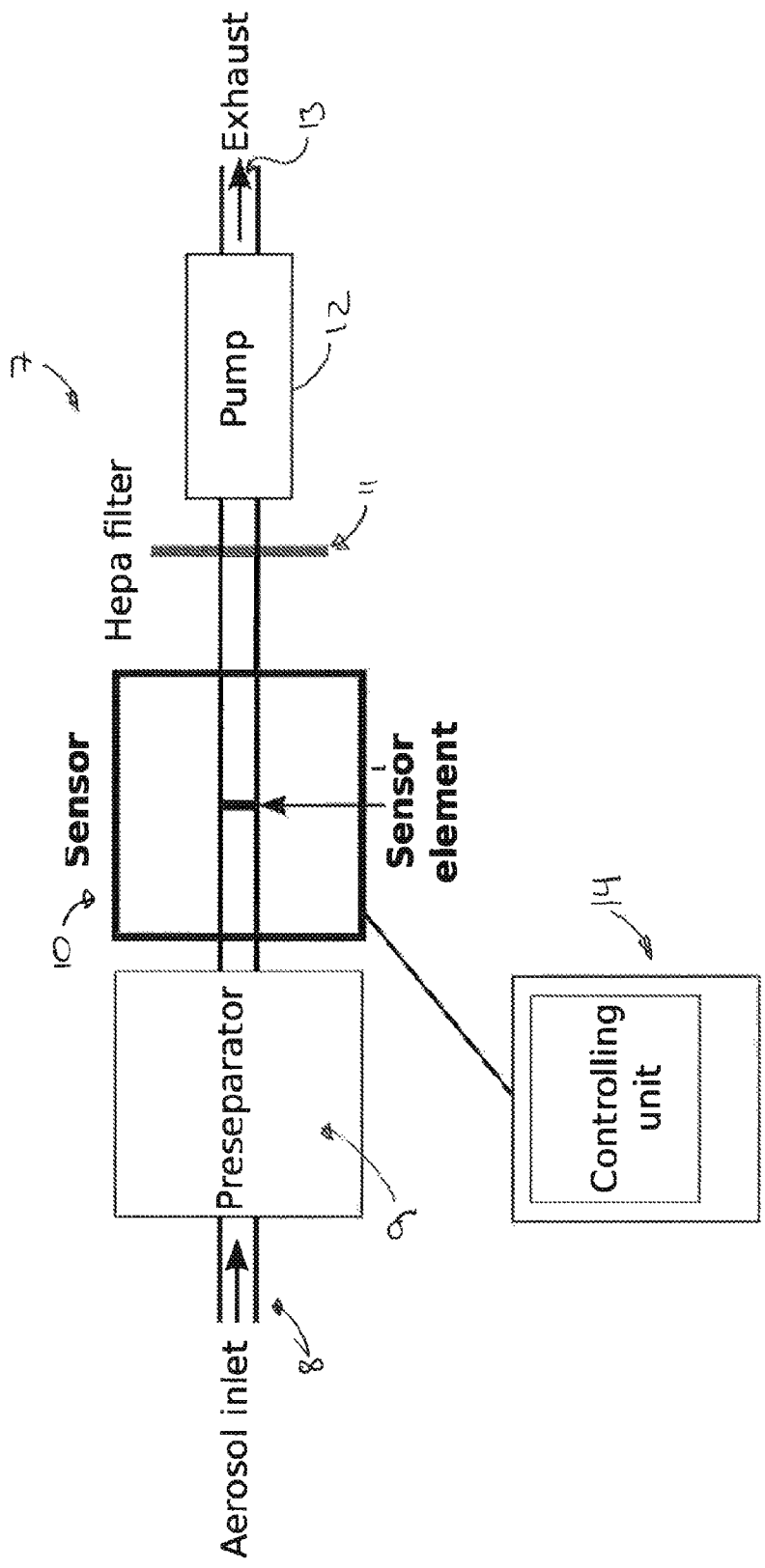
FIG. 5 shows schematically a measuring device according to the present invention employing a sensor element according to the present invention.

The elongate member(s) may be vibrated in different resonance modes. There are two distinct modes, the flexural mode and the bulk mode. FIG. 5 shows an example of bulk mode. In the bulk mode, the elongate member will normally be fixed in a nodal point and the elongate member expands and contracts in its longitudinal direction, while there is no movement at the nodal point and no movement out of the plane defined by the elongate member. For the flexural mode, the fixation could also be at the nodal points.

In general, the vibration according to the present invention is not limited to a particular vibration mode or direction. For instance, the direction of flexural vibration of the elongate member could be in the direction of the fluid flow, transversely thereto or even in a combination mode thereof.

Typical and preferred transducers used for readout include: electrostatic, magnetic, magneto-motive, piezo-electric, piezo-resistive, optical transducers.

Typical and preferred transducers used for actuation include: electrostatic, magnetic, piezo-electric, thermal, acoustic transducers.

Various types of actuation and detection (readout) included in the invention are, e.g.:
1. Magnetic actuation and magneto-motive readout, typically, for elongate members vibrating in the bending mode and being attached at both distal ends (Lorentz-force)
2. Thermal actuation and piezo-resistive readout
3. Piezoelectric actuation and piezo-resistive readout
4. Magnetic actuation and piezo-resistive readout
5. Any actuation and optical readout frequency.
6. Electrostatic actuation and readout, typically, for elongate members vibrating in the longitudinal bulk mode
7. Acoustic actuation by exposing the elongate member to sound waves.

Other combinations are considered within the scope of the invention. Particular preferred combinations of actuation and transduction are disclosed below.

Magnetic Actuation & Magnetomotive Readout

The magnetomotive technique is applicable for the transduction of conductive elongated members being attached at one end only and at both ends. It is easily implementable and is applicable over a high frequency range from 0 up to the GHz range. In this technique, the elongate member 4 is placed in a high magnetic field perpendicular to longitudinal extension of the elongate member 4. For actuation, a Lorentz-force is generated if an oscillating current is passed through the beam. The resulting flexural displacement of the beam, traveling through the magnetic field, generates an electromotive force, resulting in a voltage over the length of the beam. The beam displacement can be measured by sensing this voltage. Attention has to be paid to the fact that only odd resonant bending modes can be transduced with this technique. In even modes, the induced net voltage is zero. The strong magnetic field with a field strength in the Tesla range can simply be achieved by e.g. a Halbach array.

Piezoresistive Readout

In piezoresistive sensing elongate member 4 has an integrated resistor which has piezoresistive properties. Due to the piezoresistive property the resistance changes when the beam bends. Thus, by an electrical measurement of a resistance change the deflection of the beam can be determined. The benefits of this method are that the principle works well in both liquid and gas phase and large arrays of elongate members 4 can be realized and read-out. Also, the technique is applicable for static as well as dynamic measurements. Metal, such as gold, is found to be particular applicable as a strain gauge integrated in elongate member 4, however silicon is also found application. Even though the gauge factor of gold is low the final frequency resolution is high because of the low electrical noise in the gold film. Furthermore, the integrated gold electrode allows a perfect impedance matching with standard electronic equipment such as network analyzers which typically use 50 ohm. Thus, the signal transfer from the elongate member 4 is very efficient.

Thermal Actuation

The elongate member 4 can be actuated by local pulsed heating. In particular preferred embodiments the elongate member 4 is a bimorph member and the heating causes a deflection due to the different thermal expansion of the different layers. In an elongate member being attached at both ends, a pulsed heating causes a modulation of the tensile stress resulting in a parametric actuation. Optical heating is often combined with an external optical readout and allows a fully external transduction of nanomechanical systems. Local heating can also be integrated by a resistive heating element.

If the detection technique is designed to be sensitive enough and the noise level is lower than that of the thermal noise of the resonator, the thermal noise resonance peaks can be detected directly.

Optical Readout

Optical transduction methods can either be fully external (not being part of the sensor element 1) or integrated (forming part of the sensor element 1). External techniques, such as interferometry, laser-Doppler vibrometry, optical leverage readout and radiation pressure actuation have the advantage that no physical connection to the vibrating elongated member 4 is required with the exception of the access for the laser beam. In optical waveguide end-coupling, evanescent light coupling and Mach-Zehnder interferometry the optical transduction is fully integrated on-chip. Besides the coupling of an external fiber to the sensor element 1, integrated techniques need no alignment of laser beam and nano resonator and compared to the external techniques are not limited by the diffraction of light.

Optical vibrometry is based on the Doppler-effect; sensing the frequency shift of back scattered light from a moving surface via optical interference. Because the frequency shift is caused by the Doppler-effect, the modulation frequency of the interferometer pattern is directly proportional to the velocity of the object.

Optical leverage is a commonly used read-out system known from atomic force microscopy and is often used for the static and dynamic readout of micro cantilevers. A laser is focused on the back of a cantilever. The reflected light is then detected by a position sensitive photo-detector. A drawback is the difficult alignment of the laser such that it hits the photo-detector after having been reflected on the nano resonator. Furthermore, the resonator usually requires a reflective coating.

End-coupled waveguide is a detection method, where the elongate member 4 acts as a waveguide that couples at its end to another waveguide. When the waveguide-cantilever is vibrating, it changes the coupling efficiency (transmission) which results in an optical amplitude modulation.

Hard-Contact Readout (Door Bell Design)

The detection of resonant frequencies of elongate members 4 has been performed by tunneling and by hard contact read-out. In tunneling read-out the elongate member 4 is placed in close proximity to a counter electrode and the tunneling current between the electrode and the cantilever is measured. In hard contact read-out the elongate member 4 is allowed to touch the electrode and the current running through the system is measured. The large current at resonance makes the read-out nearly digital and the quality of the signal amplification is not as important.

Capacitive Readout and Actuation

Two electrodes separated by any material or air/vacuum have a capacitance and this capacitance changes when the distance between the electrodes changes. If an elongate member 4 is placed close to an electrode or two electrodes, the movement of the member 4 relative to the electrode will cause a capacitance change which can be measured. Between the beam and the electrode there also exists an attractive force which can be used for actuation. Capacitive read-out has the advantage of offering an integrable read-out which does not influence the elongate member 4 itself. No additional layer needs to be added with the risk of degrading the cantilevers' mechanical performance.

Field Emission Detection

For this technique, a vibrating rod is mounted to an electrode in close proximity to a counter electrode and a dc bias voltage is applied. The applied voltage induces a constant field emission current which is modulated by the mechanical vibration of the resonating elongate member 4 which can easily be measured.

Piezoelectric Readout and Actuation

Piezoelectricity has been widely used for both beam actuation and for detection of beam deflection. Basically, a mechanical stress generates an electrical potential across a piezoelectric material and vice versa. For high resolution detection of the deflection it is necessary to operate the elongate member in the dynamic mode since the voltage produced by a static force cannot be maintained by the thin film piezoelectric material. Thus, the piezoelectric read-out is primarily utilized in resonance mode. The most commonly used piezoelectric material used in micro and nanomechanical resonators is zinc oxide and aluminium nitride.

Thus, the resonance frequency is determined by a sensor which together with the actuator is connected to a controlling unit 14 (see e.g. FIG. 5). The controlling unit 14 may be in the form of an ordinary computer comprising software adapted to control peripheral equipment adapted to control the actuator and providing readouts from the transducer. Alternatively, the controlling unit 14 may be a tailored electronic unit.

One of the promising features of the present invention is that the elongate member 4 extends from the base element 2 and into a region where the aerosol may flow unhindered from other sources than the very small influence the elongate member 4 has on the flow. Thereby, inertia effects introduced e.g. by highly curved streamlines are minimised which otherwise could result in that lighter particles follow the streamlines whereas heavier ones does not, whereby only the heavier particles will deposit on the elongate member 4 introducing a measuring of particle weight being skew towards the lighter particles.

Figure 2:
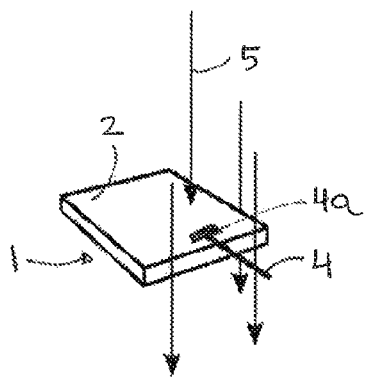
FIG. 2 shows schematically a sensor element according to a second embodiment of the invention.

FIG. 2 shows another embodiment of a sensor element 1 according to the present invention. In this embodiment, the elongate member 4 is attached at one distal end 4a to the base element 2 and extends out from the base member 2. However, in contrast to the embodiment of FIG. 1, the base member 2 does not comprise the penetration. In use, however, the sensor element 1 is arranged so that the elongate member 4 extends into a region where the aerosol may flow unhindered from other sources than the very small influence the elongate member 4 has on the flow, thus, the aerosol flows past the elongate member 4 as indicated by the arrows 5. During the aerosol's passage of the elongate member 4, aerosol particles deposit on the elongate member 4.

Figure 3:
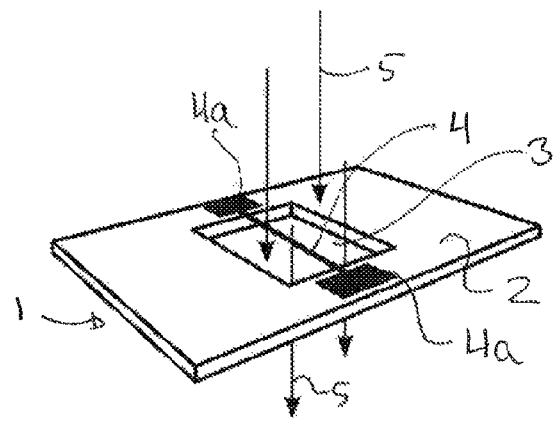
FIG. 3 shows schematically a sensor element according to a third embodiment of the invention.

In the above FIGS. 1 and 2, the elongate member 4 is attached at one distal end only as a cantilever. However, the elongate member 4 may, according to the invention, be attached to a base element 2 at both distal ends. One such example is shown in FIG. 3. The sensor element 1 of FIG. 3, comprising a base element 2 having a penetration 3 and the elongate member 4 is attached to the base element 2 at its distal ends and extends across the penetration 2. The aerosol flow is directed through the penetration 2 as disclosed in connection with FIG. 1. During the aerosols passage of the penetration, aerosol particles deposit on the elongate member as disclosed above in connection with FIG. 1.

Figure 4:
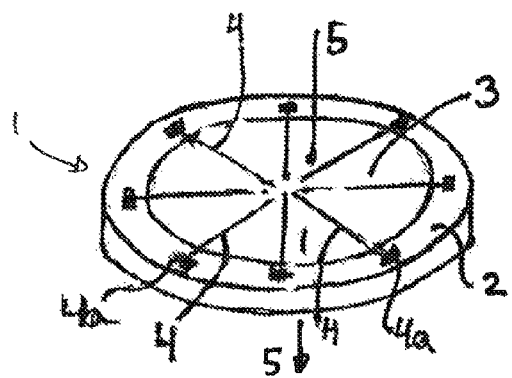
FIG. 4 shows schematically a sensor element according to a fourth embodiment of the invention.

In the above FIGS. 1, 2 and 3, the penetration and the base element are shown exemplified with rectangular geometries. However, the penetration 3 and the base element may be given other shapes such as circular. One such example is shown in FIG. 4 in which the base element 2 is circular shaped with a circular shaped penetration 3. The elongate members 4 (eight is shown) extend from the base element 2 along radius towards the centre of the circular shaped penetration 3.

Figure 6:
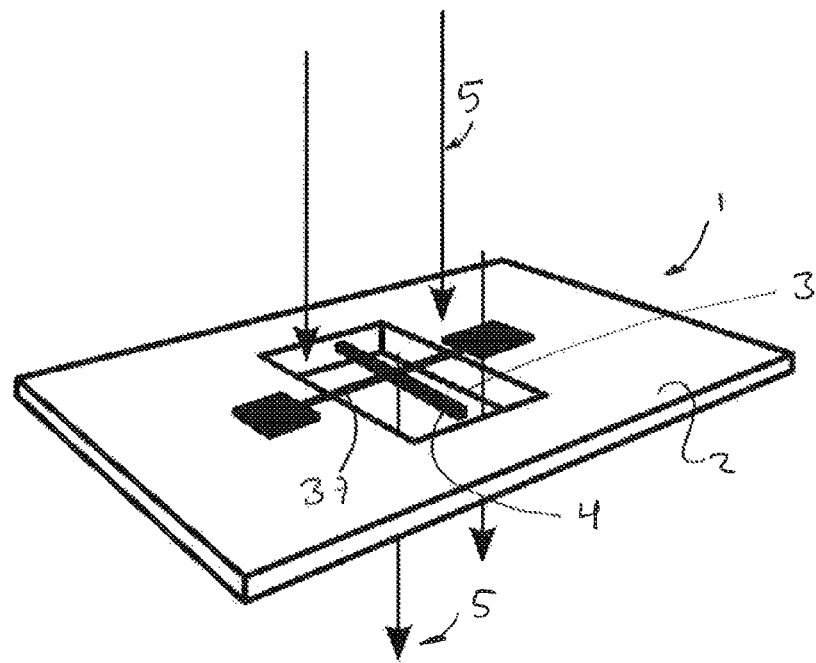
FIG. 6 shows schematically a sensor element according to a fifth embodiment of the invention.

In FIG. 6, a sensor element design is shown where the elongated member 4 is attached at a nodal point of the mechanical displacement. The elongate member 4 is attached to the base member 1 through a mechanical connection 37 in the form of elongate member. This design is preferably used for case in which the elongate member 4 is vibrating in the longitudinal bulk mode instead of in a bending mode. The elongate member can also be attached to the base element at the nodal points when vibrating in a bending mode.

Figure 8A:
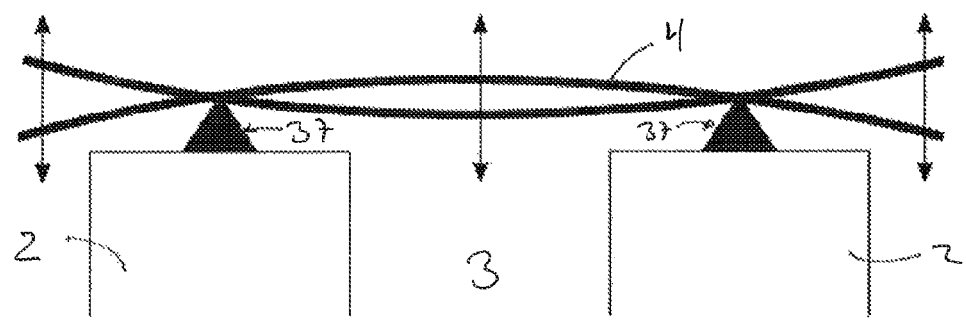
Figure 8B:
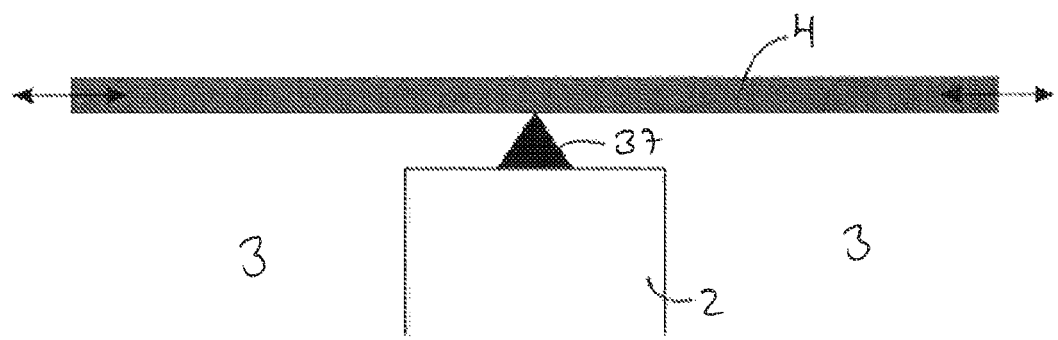

In a slightly modified embodiment of FIG. 6 (not shown), the elongate member 4 is attached at the nodal point(s) to the base member 1 by a connection 37 allowing the elongate member to vibrate without interference from the base member 1. Two such examples are shown in FIGS. 8a and 8b. FIG. 8a shows a free-free bending mode. and FIG. 8b shows a longitudinal bulk mode. As indicated in FIG. 8, the elongate member 4 is attached to the base element 2 by connections 37 allowing the vibrational form indicated. The arrows in the figures show the vibration of the elongate member 4 and numeral 3 indicates a penetration—or in general a void—similarly to the disclosure presented herein with respect to the other embodiments of the invention.

The elongate member 4 is typically and preferably produced by using a micro fabrication being well known to a skilled person. The production method typically and preferably comprising one or more of the following processes:

Standard micro fabrication: depositing of the material of the elongate member 4, (preferably being selected from the group consisting of silicon nitride, silicon, silicon carbide, silicon oxide, SU-8, nickel, aluminium, gold, or similar materials) on a silicon wafer being photo-lithographically defined and etched by means of dry or wet etching process, Macroscopic thinning: Macroscopic fibers (silicon oxide, metals or polymers) are stretched until they reach the desired diameter of elongate member 4 and is/are then fixed onto a base element 2.

Bottom-up process. The elongate member 4 is grown directly on the base element 2, e.g. as carbon nanotubes or nanowires.

All the production methods may include coating the elongate member 4 with a conductive layer.

FIG. 5 shows schematically an embodiment of a measuring device 7 according to the present invention. The measuring device 7 preferably employs a sensor element 1 according to the present invention. The measuring device 7 comprising (as seen from in a downstream direction) an aerosol inlet 8, a pre-separator, typically in the form of an impactor, cyclone or other gravitational separation device, a sensor 10 including the sensor element 1, a HEPA filter 11, a pump 12 and an exhaust 13. The measuring device 7 forms a closed unit in the sense that the fluid enters the device 7 through inlet 8, flows through the various parts of the device 7 in a sequentially manner and leaves the device 7 through exhaust 13 only. The sensor 10 comprises one or more sensor elements 1, actuators and detectors as disclosed above. In the figures, it is indicated that the pump 12 is arranged downstream of the sensor 10, however, the pump 12 may be arranged upstream of the sensor 10.

Aerosol is sucked by means of the pump 12 into the measuring device 7 through the aerosol inlet 8 and flows into the pre-separator 9. In the pre-separator, larger particles are separated off, so that the aerosol going into the sensor 10 does not contain such larger particles. Thus, the pre-separator 9 may be seen as having a cut-off limit and particles being larger than the cut-off limit are separated off in pre-separator 9. The cut-off limit and thereby also the design of the pre-separator 9 are selected in accordance with a particular intended use and the characteristics of the aerosol. For instance, a cut-off limit of 300 nm is often found particular useful e.g. in order to only detect the nanotoxicologically relevant nanoparticles and to dismiss the nanotoxicological lesser relevant larger particles.

During the aerosol's passage of the sensor 10, some of the particles deposit on the elongate member 4 of the sensor element 1 arranged inside the sensor 10 resulting in a change in resonance frequency as disclosed herein. After passage of the sensor 10, the aerosol flows through an optional HEPA filter 11 to filter of particles and leaves the measuring device 7 after passage of the pump 12 through the exhaust 13. The exhaust 13 is typically connected to the ambient but may lead the aerosol to a storage reservoir if so desired.

The measuring device 7 is connected to or comprising computer means receiving readouts from the detector, controlling the actuator and controlling the pump 12 to generate a desired flow of aerosol through the measuring device. The computer means comprising a processor, memory and instructions enabling the computer means to determine weight based on the readout from the detector.

The total mass of a number of particles deposited on the elongate member or the mass of a single particle deposited on the elongate member is calculated from the frequency downshift of a calibrated sensor 1. The total mass can be determined based on the readout from the vibration of the elongate member 4 e.g. from the first, second, or higher resonant bending mode or bulk mode etc. of the resonating elongate member 4. The mass of individual particles can be computed based on the frequency shift of higher order bending or bulk modes.

Eventhough that the invention has proven not to be sensible to the distribution of particles deposited on the elongate member, it is preferred to obtain an even distribution of particles. This could e.g. be ensured by assuring a uniform flow of aerosol past the elongate member (it is assumed, of course, that the particles of in the aerosol are evenly distributed).

During use of the sensor 1, particles will as desired deposit on the elongate member(s) 4. Although such depositing is as desired, it results over time in that the elongate member(s) 4 is saturated with particles (no substantial readout is obtainable to determine frequency shifts) which in turn renders the elongate member(s) 4 less effective or even useless. Due to the delicate nature of the elongate member(s) 4, cleaning of the elongate member(s) 4 is often not an option as this could destroy the elongate member(s) 4.

Devices according to the present invention therefore often house the sensor element 1 in a manner where it can be replaced by a new sensor element 1; thus, the sensor element 1 is a separate, replaceable element of the measuring device 7. Thereby the sensor element 1 can be extracted from the measuring device 7 when the sensor element 1 is saturated with particles and a new sensor element 1 is inserted into the measuring device 7.

Figure 7:
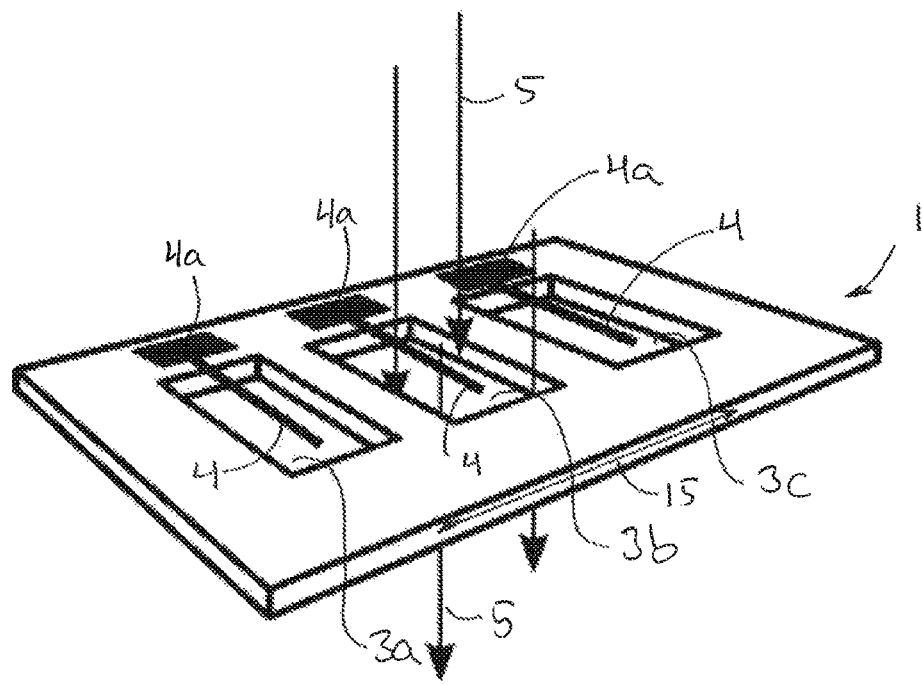
FIG. 7 shows schematically a further embodiment of a sensor element having three elongate members each arranged above a separate penetration, FIG. 8a,b shows schematically various vibrations mode employed by the present invention.

Alternatively or in combination thereto, devices 7 may be configured by individually addressing only some elongate member(s) 4 of a sensor at a time. Thus, once one or more elongate member(s) become saturated with particles, other elongate members(s) 4 are addressed. Such addressing is typically implemented by suitable aerosol guides, guiding aerosols to selected elongate member(s) 4 at a time only. Another approach is to displace the sensor 1 internally into a flow channel of the measuring device 7 so that only some of the elongate member(s) 4 are exposed in the flow channel. An embodiment useful in this connection is shown in FIG. 7. The sensor element 1 comprising three penetrations 3a, 3b and 3b each having an elongate member 4 extends in straight manner out from the base member 2, so as to not extend along and above the surface of the base member 2—as disclosed also in relation to FIGS. 1-4, 5-6. During use, the sensor element 1 is arranged so that only one of the elongate members 3 is exposed to the flow of aerosol. Once the elongate member is saturated, the sensor element is displaced so that the saturated member 3 is no longer in use, but a not yet saturated elongated member 1 is exposed to the flow of aerosol, e.g. by shifting the position of the sensor element 1 along the arrow marked 15 in FIG. 7. The number of penetrations can be more than 3 as shown in FIG. 7.

The above disclosure pertaining to replacing the sensor element 1 is based on the detector and/or actuator being separate from the sensor element 1. If this is not the case, the detector and/or actuator is replaced with the sensor element 1. In addition, it may be feasible to replace the sensor 10 including the sensor element 1, the actuator and the detector as a unit.

Preferably, the resonance is determined by measuring the vibrational amplitude or certain frequency band width, the resonance frequency is the given at the maximum amplitude. In the case of driving the elongate member in a feed-back controlled oscillation, the resonance frequency corresponds to the oscillating frequency. Another way utilises the burst mode actuation and the resonance frequency is determined from the amplitude ring-down.

Further aspects and embodiments of the present invention relates to an initial coating of an elongate member 4 with a substance to e.g. functionalise the surface of the elongate member 4. The initial coating is performed by depositing a specific substance in the form of nano-particles on the surface of the elongate member 4 by a method as disclosed herein wherein the aerosol is manufactured to contain the specific substance.

The aerosol is produced by atomizing (put in airborne state) nano-particles desired to be deposited on the elongate member 4 and depositing such nano-particles on the surface of the elongate member 4 by the methods disclosed herein. This deposition will increase the total surface area of the elongate member 4. The nanoparticles are sticking to the surface naturally by Van-der-Waals or electrostatic forces and do not require any further fixation. Once the particles are deposited on the elongate member 4, this elongate member is ready to be used as e.g. a functionalised elongate member 4. As an example of a functionalised elongate member (4) is an elongated member 4 upon which nano-particles of polymer are deposited which increase the uptake of a chemical analyte due to the gained enhanced surface area of the nano-particles. This increased absorption or adsorption of a chemical analyte increases the sensitivity of the elongate member 4 to the chemical analyte.

Another aspect and embodiment of the present invention relates to the use of the present invention to collect/sample nano-particles on the elongate member 4 for a subsequent characterization of the collected nano-particles sitting on the elongate member 4 by other techniques (e.g. absorption spectroscopy, Raman spectroscopy, scanning electron microscopy, transmission electron microscopy, etc.) allowing for a chemical or physical characterization of the nano-particles on the elongate member 4.

Experimental Results

Figure 10:
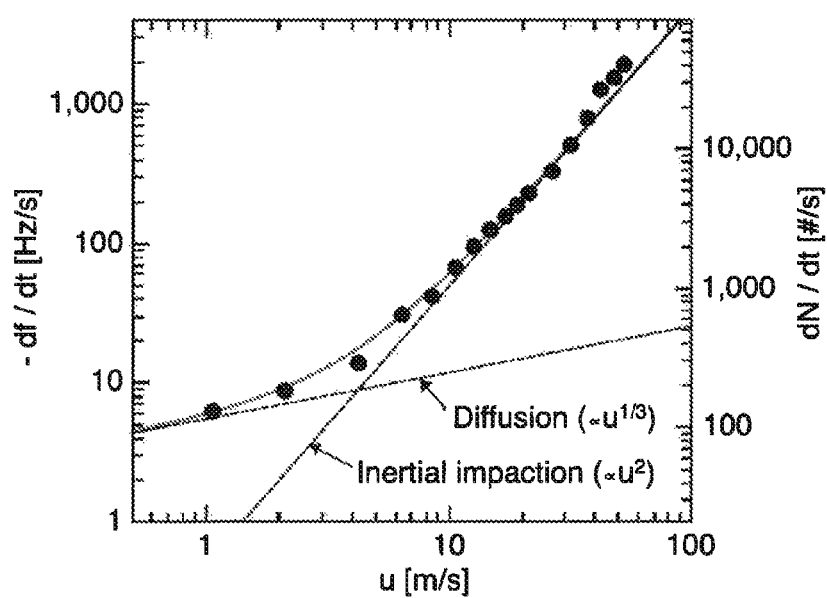
FIG. 10 shows experimental results obtained with an embodiment of the present invention.

In FIG. 10 results obtained with an embodiment of the present invention is presented. FIG. 10 shows in particular the response of an elongated member 3 being 3 µm wide (measured perpendicular to the direction of the incoming flow), 138 µm long (measured in between the position where it is attached to the base member at both ends) and 220 nm thick (measured in the streamvise direction of the incoming flow). The elongate member 3 is made of silicon nitride coated with 50 nm aluminium.

The aerosol flowing towards and past the elongated member 3 contains 28.0±3.2 nm silica nanoparticles with a concentration of $3\times10^6\pm1\times10^6$ particles/cm$^3$. FIG. 10 shows the measured frequency shift per second (df/dt) and the corresponding number of particles collected per second (dN/dt). At low aerosol velocities (u<10 m/s) the measured collection mechanism is dominated by diffusive precipitation which is proportional to $u^{\wedge}(1/3)$. At higher aerosol velocities (u>10 m/s) the measured collection mechanism is dominated by inertial impaction which is proportional to $u^{\wedge}2$. This quadratic velocity proportionality of the nano-particle collection efficiency due to inertial impaction makes this the preferred collection mechanisms. At higher aerosol velocities (u>10 m/s), nano-particles gain enough momentum to leave the streamline passing around the elongate member, thereby impacting on the elongate member.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A method for determining the weight of aerosol particles, the method utilises a sensor system comprising a sensor element comprising a base member, one or more elongate members, an actuator for driving the one or more elongate members into resonance, and a detector for determining the vibration frequency of the one or more elongate members, wherein
   each of the one or more elongate members are made from an elastic material with a longitudinal extension, being at least ten times the diameter or the equivalent diameter of the cross section of the elongate member, the diameter or equivalent diameter being in range of 1 nm-100 µm,
   each of the one or more elongate members being attached at least at one end to the base member or at a nodal point of the vibrational displacement through a connection and extends in a straight manner out from the base member, so as not to extend along and above the surface of the base member,
   the method comprising the step of
   producing a flow of aerosol past one or more of the elongate members in an oblique direction, such as perpendicular, to the longitudinal direction of the elongate member, wherein:
   the velocity of the aerosol is higher than 1 m/s, and/or
   one or more of the elongate members being electrostatic charged
   vibrating and detecting vibration frequency of the elongate member by use of the actuator and detector, so as to determine the resonance frequency, and
   determining the weight of the aerosol particles from the detected resonance frequency,
   wherein
   the sensor system comprises a region immediate downstream of the elongate member(s) devoid of obstacles, the extension of said region being at least 100-1,000 diameters or equivalent diameters of the elongate member(s).

2. A method according to claim 1, wherein the velocity of the aerosol is higher than 4 m/s or higher than 8 m/s, or higher than 10 m/s, or higher than 15 m/s, or higher than 25 m/s.

3. A method according to claim 1, wherein the velocity of the aerosol is lower than 1000 m/s, or lower than 500 m/s, or lower than 100 m/s.

4. A method according to claim 1, wherein the elongate member(s) is(are) arranged in a region of the flow of aerosol where the flow of aerosol being at least substantially free-streaming.

5. A method according to claim 1, wherein one or more elongate members are attached to the base member at one end only, thereby constituting a cantilever beam.

6. A method according to claim 1, wherein one or more of the elongate members are attached to the base member at both ends.

7. A method according to claim 1, wherein one or more of the elongate members are attached at one or more nodal points.

8. A method according to claim 1, wherein the elongate member comprises piezo-electric and/or piezo-resistive elements and that the piezo-electric and/or piezo-resistive elements constitute at least a part of the actuator and/or detector, and/or the elongate member comprises thermal elements, optical reflectors, conductive part for capacitive or magnetic actuation.

9. A method according to claim 1, wherein the base member comprising a penetration, forming a flow passage of the sensor element, the one or more elongate members extends across the penetration.

10. A method according to claim 1, wherein the sensor element, comprising a plurality of elongate members all extending in parallel to each other.

11. A method according to claim 1, wherein the method further comprises a deposition of nano-particles on the elongate member in order to facilitate a functionalization of the elongate member with specific nano-particles, the deposition comprising:
   producing a flow of aerosol containing a selected composition of nano-particles past one or more of the elongate members in an oblique direction, such as perpendicular, to the longitudinal direction of the elongate member, wherein:
   the velocity of the aerosol is higher than 1 m/s, and/or
   one or more of the elongate members being electrostatic charged.

12. A method according to claim 1, wherein the method further comprises a deposition of nano-particles on the elongate member in order to facilitate a subsequent chemical or physical characterization of the nano-particles collected on the elongate member by non-gravimetric techniques for the deposition comprising:
   producing a flow of aerosol containing a selected composition of nano-particles past one or more of the elongate members in an oblique direction, such as perpendicular, to the longitudinal direction of the elongate member, wherein:
   the velocity of the aerosol is higher than 1 m/s, and/or
   one or more of the elongate members being electrostatic charged.

13. A through flow measuring device for measuring weight of aerosol particles contained in an aerosol flowing through the device, the device comprising a sensor through which the aerosol flows,
   the sensor being arranged downstream of an inlet of the measuring device and the measuring device comprising a flow channel extending through the sensor, the sensor comprising one or more elongate members, an actuator for driving the one or more elongate members into resonance, and a detector for determining the vibration frequency of the one or more elongate members so as to determining the resonance frequency, each of the elongate members extending out from the boundaries of the flow channel in an oblique direction, such as perpendicular, to the flow direction of the fluid during use, and
   the flow channel being adapted to produce a parallel flow in the aerosol past the elongate member, and comprises a region immediate downstream of the elongate member(s) devoid of obstacles, the extension of said region being at least 100-1,000 diameters or equivalent diameters of the elongate members,
   wherein the sensor comprises one or more sensor elements each having a sensor element comprising a base member, one or more elongate members, an actuator for driving the one or more elongate members into resonance, and a detector for determining the vibration frequency of the one or more elongate members, wherein each of the one or more elongate members are made from an elastic material with a longitudinal extension, being at least ten times the diameter or the equivalent diameter of the cross section of the elongate member, the diameter or equivalent diameter being in range of 1 nm-100 µm, each of the one or more elongate members being attached at least at one end to the base member or at a nodal point of the vibrational displacement through a connection and extends in a straight manner out from the base member, so as not to extend along and above the surface of the base member, and wherein the sensor element(s) is received in the sensor in an exchangeable manner.

14. A through flow measuring device according to claim 13, wherein sensor comprising a plurality of elongated members, and the measuring device being adapted to individually addressing only some elongate member(s) at a time by allowing the fluid to contact the only some of the elongate members at a time.

15. A through flow measuring device according to claim 13, further comprising a pre-separator arranged upstream of the sensor to separate out from the aerosol particles having a size greater than a given size, the given size is preferably larger than 300 nm or larger than the diameter of the elongate member in any case.

16. A through flow measuring device according to claim 13, further comprising a pump arranged upstream or downstream of the sensor for forcing the fluid through the measuring device, the pump being adapted to produce a velocity of the fluid higher than 1 m/s.

17. A through flow measuring device according to claim 13, further comprising a filter, preferably a HEPA filter downstream of the sensor and upstream of an exhaust of the measuring device.

18. A through fluid measuring device according to claim 13, further comprising control means for controlling actuator, the detector, and when dependent on claim 11, the operation of the pump.

19. A method according to claim 1 or a through flow measuring device according to claim 13, wherein the actuator is selected from the group consisting of electrostatic, magnetic, thermal, piezoelectric, acoustic actuator being adapted to vibrate the one or more elongate members, preferably at frequency between 10 Hz and 10 GHz, or between 100 Hz and 1 GHz.

20. A method according to claim 1 or a through flow measuring device according to claim 13, wherein the detector comprises a transducer selected from the group consisting of electrostatic, magnetic, magneto-motive read-out, piezo-resistive, piezo-electric readout, or optical and being adapted to detect vibration of the one or more elongate members at a frequency between 10 Hz and 10 GHz or between 100 Hz and 1 GHz.

* * * * *